(12) United States Patent
Kiya et al.

(10) Patent No.: US 9,847,528 B2
(45) Date of Patent: Dec. 19, 2017

(54) PREDOPING MATERIAL, ELECTRIC STORAGE DEVICE INCLUDING THE MATERIAL, AND METHOD OF PRODUCING THE DEVICE

(71) Applicant: Fuji Jukogyo Kabushiki Kaisha, Tokyo (JP)

(72) Inventors: Yasuyuki Kiya, Tokyo (JP); Takahito Sakuraba, Tokyo (JP); Satoru Kudo, Tokyo (JP); Ken Baba, Tokyo (JP)

(73) Assignee: SUBARU CORPORATION, Tokyo (JP)

( * ) Notice: Subject to any disclaimer, the term of this patent is extended or adjusted under 35 U.S.C. 154(b) by 603 days.

(21) Appl. No.: 14/226,282

(22) Filed: Mar. 26, 2014

(65) Prior Publication Data

US 2014/0292281 A1 Oct. 2, 2014

(30) Foreign Application Priority Data

Mar. 29, 2013 (JP) .................................. 2013-073776

(51) Int. Cl.
*H02J 7/00* (2006.01)
*H01M 4/583* (2010.01)
(Continued)

(52) U.S. Cl.
CPC .......... *H01M 4/583* (2013.01); *C07C 321/04* (2013.01); *C07C 321/26* (2013.01); *C07D 251/38* (2013.01); *C07D 317/36* (2013.01); *H01M 4/131* (2013.01); *H01M 4/133* (2013.01); *H01M 4/136* (2013.01); *H01M 4/1391* (2013.01); *H01M 4/1397* (2013.01); *H01M 4/386* (2013.01); *H01M 4/387* (2013.01); *H01M 4/587* (2013.01); *H01M 4/62* (2013.01); *H01M 10/049* (2013.01); *H01M 10/052* (2013.01); *H01M 10/054* (2013.01); *H01M 10/058* (2013.01);
(Continued)

(58) Field of Classification Search
CPC .................................................. H01M 10/0562
USPC ......................................................... 320/137
See application file for complete search history.

(56) References Cited

U.S. PATENT DOCUMENTS 4,485,155 A * 11/1984 Holl et al. ..................... 429/338
4,804,594 A * 2/1989 Jow et al. ...................... 429/213
(Continued)

FOREIGN PATENT DOCUMENTS

CN 101160684 A 4/2008
CN 101218705 A 7/2008
(Continued)

OTHER PUBLICATIONS

Japanese Office Action dated Oct. 18, 2016 issued in corresponding Japanese Patent Application No. 2013-073776.
(Continued)

*Primary Examiner* — Suchin Parihar
(74) *Attorney, Agent, or Firm* — Troutman Sanders LLP

(57) ABSTRACT

A predoping material is used for an alkali metal ion electric storage device and is represented by Formula (1):

$$R\!-\!(\!SM)_n \qquad (1)$$

where M represents lithium or sodium; n represents an integer of 2 to 6; and R represents an aliphatic hydrocarbon, optionally substituted aromatic hydrocarbon, or optionally substituted heterocycle having 1 to 10 carbon atoms).

13 Claims, 6 Drawing Sheets

☐ : Li ION OCCLUSION/EMISSION SITE CAPABLE OF PARTICIPATING IN CHARGE/DISCHARGE REACTION
▨ : NOVEL PREDOPING (PD) MATERIAL
▱ : Li ION SITE TO BE IRREVERSIBLY CONSUMED FOR FORMING FILM
▬ : USELESS Li ION SITE NOT CAPABLE OF PARTICIPATING IN CHARGE/DISCHARGE REACTION
▦ : POSITIVE ELECTRODE PROTECTING FILM (AFTER CHARGE REACTION)

(51) Int. Cl.

| | | |
|---|---|---|
| C07D 251/38 | (2006.01) | |
| H01M 4/131 | (2010.01) | |
| H01M 4/136 | (2010.01) | |
| H01M 4/1391 | (2010.01) | |
| H01M 4/1397 | (2010.01) | |
| H01M 4/38 | (2006.01) | |
| H01M 4/587 | (2010.01) | |
| H01M 4/62 | (2006.01) | |
| H01M 10/04 | (2006.01) | |
| H01M 10/052 | (2010.01) | |
| H01M 10/054 | (2010.01) | |
| H01M 10/0567 | (2010.01) | |
| H01M 10/058 | (2010.01) | |
| H01M 10/44 | (2006.01) | |
| H01M 4/133 | (2010.01) | |
| C07D 317/36 | (2006.01) | |
| C07C 321/04 | (2006.01) | |
| C07C 321/26 | (2006.01) | |
| H01M 4/36 | (2006.01) | |

(52) U.S. Cl.
CPC ..... *H01M 10/0567* (2013.01); *H01M 10/446* (2013.01); *H01M 4/366* (2013.01); *H01M 2300/0025* (2013.01)

(56) References Cited

U.S. PATENT DOCUMENTS

| | | | | |
|---|---|---|---|---|
| 6,506,524 | B1* | 1/2003 | McMillan et al. | 429/324 |
| 2009/0234088 | A1* | 9/2009 | Takemoto | C08F 212/14 526/271 |
| 2010/0248041 | A1* | 9/2010 | Kikuchi et al. | 429/342 |
| 2012/0175761 | A1* | 7/2012 | Zenbutsu | 257/676 |
| 2013/0052526 | A1* | 2/2013 | Momo et al. | 429/211 |
| 2013/0078499 | A1 | 3/2013 | Casasanta | |
| 2013/0224581 | A1* | 8/2013 | Saito et al. | 429/211 |
| 2014/0021904 | A1* | 1/2014 | Takahashi et al. | 320/107 |
| 2014/0023922 | A1* | 1/2014 | Isshiki et al. | 429/211 |
| 2014/0099558 | A1* | 4/2014 | Itakura et al. | 429/336 |
| 2014/0186663 | A1* | 7/2014 | Hiroki | H01M 10/52 429/57 |
| 2015/0099193 | A1* | 4/2015 | Hamasaki et al. | 429/338 |
| 2015/0380729 | A1* | 12/2015 | Kojima et al. | 429/211 |

FOREIGN PATENT DOCUMENTS

| | | |
|---|---|---|
| EP | 2400588 A1 | 12/2011 |
| JP | H08-138742 A | 5/1996 |
| JP | 2000-215910 A | 8/2000 |
| JP | 2002-198089 A | 7/2002 |
| JP | 2005-063805 A | 3/2005 |
| JP | 2005-085633 A | 3/2005 |
| JP | 4161400 B2 | 10/2008 |
| JP | 2010-102841 A | 5/2010 |
| JP | 2012-028225 | 2/2012 |
| JP | 2012-033372 A | 2/2012 |

OTHER PUBLICATIONS

Jarvis, C.R. et. al., "A prelithiated carbon anode for lithium-ion battery applications" J. Power Sources, 162 pp. 800-802 (2006).

Shanmukaraj, D. et. al., "Sacrificial salts: Compensating the initial charge irreversibility in lithium batteries" Electrochem. Chmmun. 12 pp. 1344-1347 (2010).

Chinese Office Action dated May 4, 2017 during the prosecution of corresponding Chinese Patent Application No. 201410120498 with machine English Translation.

Rodriguez-Calero et al., "Electrochemical and Computational Studies on the Electrocatalytic Effect of Conducting Polymers toward the Rodox Reactions of Thiadiazole-Based Thiolate Compounds," J. Phys Chem. C 2010, 114, 6169-6176.

Japanese Office Action dated Jun. 20, 2017 during prosecution of corresponding Japanese Patent Application No. 2013-073776 with machine English Translation.

* cited by examiner

☐ : Li ION OCCLUSION/EMISSION SITE CAPABLE OF PARTICIPATING IN CHARGE/DISCHARGE REACTION

▨ : Li ION SITE TO BE IRREVERSIBLY CONSUMED FOR FORMING FILM

▪ : USELESS Li ION SITE NOT CAPABLE OF PARTICIPATING IN CHARGE/DISCHARGE REACTION

Background Art

PREDOPING MATERIAL, ELECTRIC STORAGE DEVICE INCLUDING THE MATERIAL, AND METHOD OF PRODUCING THE DEVICE

CROSS REFERENCES TO RELATED APPLICATIONS

The present application claims priority from Japanese Patent Application No. 2013-073776 filed on Mar. 29, 2013, the entire contents of which are hereby incorporated by reference.

BACKGROUND

1. Technical Field

The present invention relates to predoping materials, in particular, a predoping material for a lithium-ion electric storage device or a sodium-ion electric storage device and relates to a electric storage device including the predoping material and a method of producing the device.

2. Related Art

In recent years, electric storage devices such as lithium-ion rechargeable batteries have been used as power sources of electric equipment and other apparatuses and are also being used as power sources of electric vehicles and hybrid vehicles). The electric storage devices such as lithium-ion rechargeable batteries are demanded to be further improved in characteristics. For example, an increase in energy density (high capacity), an increase in power density (high power), an improvement in cycle characteristics (extension of cycle life), and high safety are required.

Furthermore, sodium-ion electric storage devices have been under development. The sodium-ion electric storage devices have high energy densities comparable to those of lithium-ion electric storage devices and are excellent in cost performance because of the use of sodium, which is an abundant resource, as a raw material.

In an alkali metal ion electric storage device, charge and discharge are performed by delivery and receipt of alkali metal ions between positive and negative electrodes.

Figure 7A:
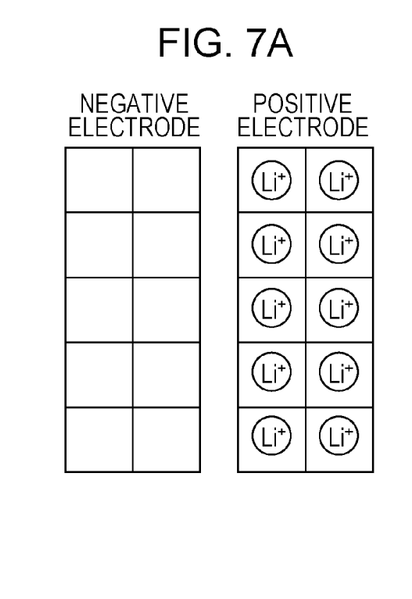
FIGS. 7A to 7C are schematic diagrams illustrating irreversible capacity occurring in a conventional alkali metal ion electric storage device.
Figure 7B:
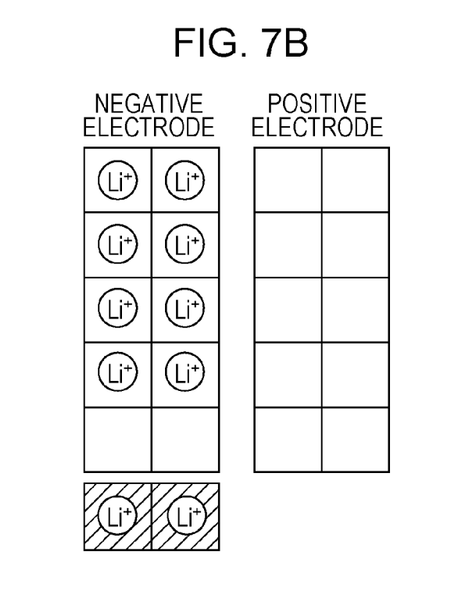
Figure 7C:
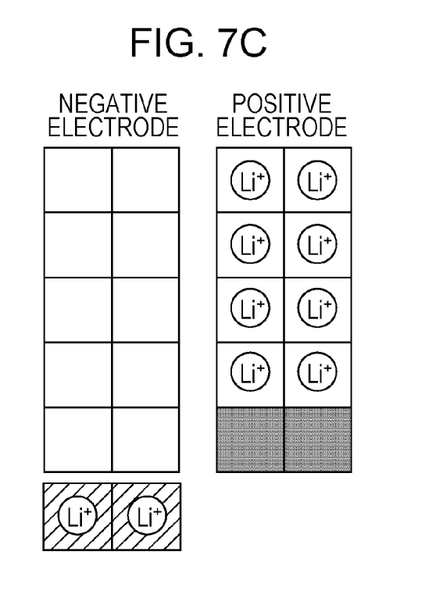

FIGS. 7A to 7C are schematic diagrams for illustrating irreversible capacity occurring in an alkali metal ion electric storage device. Herein, for convenience, as an example of the alkali metal ion electric storage device, a lithium-ion electric storage device using lithium ions as the alkali metal ion is shown, and the same explanation applies to a sodium-ion electric storage device using sodium ions.

FIG. 7A is a schematic diagram illustrating the state of lithium ions before the first charge, i.e., the state (initial state) of lithium ions at the time when a lithium-ion electric storage device has been assembled. In the initial state, all lithium ions are generally stored in the positive electrode active material, and the negative electrode active material generally does not store any lithium source and is in an undoped state.

FIG. 7B schematically illustrates the electric storage device in which lithium ions stored in the positive electrode in the initial state are emitted and are occluded in the negative electrode by the first charge. That is, the positive electrode active material is electrochemically oxidized to emit the lithium ions, and the lithium ions are occluded as charge compensation for the electrochemically reduced negative electrode active material in lithium ion storage sites of the negative electrode.

Furthermore, as shown in FIG. 7C, lithium ions are emitted from the negative electrode by discharge and are occluded in the storage sites of the positive electrode active material again.

A part of the lithium ions emitted from the positive electrode on this occasion is irreversibly consumed in the process of forming an SEI film (lithium ion conductive film) by reductive decomposition of the electrolytic solution (see shaded areas in FIGS. 7B and 7C). The lithium ions that cannot participate in the subsequent charge/discharge reaction are referred to as irreversible capacity of the negative electrode.

In general, in order to maximize the energy density of a electric storage device, the electrodes are designed in the light of the amount of lithium ions that are irreversibly consumed in the process of forming an SEI film of the negative electrode. That is, the balance in the capacity between the positive and negative electrodes is optimized. In the existent electric storage devices, however, since the irreversible capacity of the negative electrode is compensated by a lithium ion source of the positive electrode active material, a positive electrode active material that cannot participate in charge/discharge reaction is needed, resulting in a reduction in the energy density of the electric storage device.

In order to efficiently compensate the irreversible capacity of the negative electrode for improving the energy density of a electric storage device, various investigations have been performed.

For example, Japanese Unexamined Patent Application Publication (JP-A) Nos. 2005-63805 and 2005-85633 and Japanese Patent No. 4161400 describe lithium-ion rechargeable batteries in which lithium ions are occluded in the negative electrode through attachment of metallic lithium foil or vapor deposition of lithium to compensate the irreversible capacity.

C. R. Jarvis, et al., J. Power Sources, 162, p. 800 (2006), "A prelithiated carbon anode for lithium-ion battery applications" reports on the results of study for a lithium-ion rechargeable battery in which stabilized metallic lithium is added to a negative electrode to compensate the irreversible capacity of the negative electrode.

JP-A No. 2010-102841 proposes a lithium-ion rechargeable battery in which a lithium-containing complex nitride is added to a positive electrode material to compensate the irreversible capacity.

In D. Shanmukaraj, et al., Electrochem. Chmmun., 12, p. 1344 (2010), "Sacrificial salts: Compensating the initial charge irreversibility in lithium batteries", predoping with a small organic molecule having an R-OLi skeleton is performed for compensating the irreversible capacity of a lithium-ion rechargeable battery, and the effect thereof is verified.

JP-A No. 2000-215910 discloses an electrolytic solution for a lithium rechargeable battery and a lithium rechargeable battery in which the cycle characteristics are improved by adding an organic thiolate of lithium to the electrolytic solution.

However, since the lithium-ion rechargeable batteries described in JP-A Nos. 2005-63805 and 2005-85633 and Japanese Patent No. 4161400 use metallic lithium for predoping, a risk that fine powder of metallic lithium remains after the predoping is high. Thus, they have a problem in safety.

The stabilized lithium powder presented in J. Power Sources, 162, p. 800 (2006) is a surface-passivated specific and expensive particle material. Accordingly, the powder is not necessarily suitable for industrial application. In addition, there are restrictions such that the solvent used in production of the negative electrode must be an aprotic nonpolar solvent.

In the lithium rechargeable battery in JP-A No. 2000-215910, since monolithium thiolate is used as the predoping material, the amount of lithium ions that can be supplied by the predoping material is not particularly large, and the purpose of introduction of the predoping material is not an increase in energy density.

In Electrochem. Chmmun., 12, p. 1344 (2010), the small molecule used as the predoping material emits Li and thereby has an effect of compensating irreversible capacity, but the molecule after the Li emission is emitted as a gas, which may be a defect for the cell characteristics.

SUMMARY OF THE INVENTION

Accordingly, it is an object of the present invention to provide a predoping material for an alkali metal ion electric storage device that does not have the above-described defects in conventional technologies and simply and rapidly performs predoping without any additional production process to increase the energy density without impairing the safety, and to provide an alkali metal ion electric storage device including the predoping material and a method of producing the device.

An aspect of the present invention provides a predoping material represented by Formula (1):

R$(-$SM$)$n        (1)

where, M represents lithium or sodium; n represents an integer of 2 to 6; and R represents an aliphatic hydrocarbon, optionally substituted aromatic hydrocarbon, or optionally substituted heterocycle having 1 to 10 carbon atoms.

In the formula, R may represent a linear or branched $C_2$-$C_6$ alkane, triazine, benzene, or $C_2$-$C_6$ alkylene carbonate.

The predoping material may have a molecular weight within a range of 100 to 550.

Another aspect of the present invention provides a alkali metal ion electric storage device including: a positive electrode containing a positive electrode active material; a negative electrode containing a negative electrode active material constituted of C, Si, Sn, or Ge or an alloy containing at least one thereof; an electrolytic solution; and the predoping material.

The predoping material of the present invention may be added to the electrolytic solution.

The molar ratio of the predoping material to the electrolytic solution may be 0.04 to 0.25.

The predoping material may be added to the positive electrode material.

The ratio of the predoping material to the positive electrode active material may be 0.01% to 20% by mass. The predoping material may have a capacity density higher than that of the positive electrode active material by 50 mAh/g or more.

The predoping material may be oxidized on the positive electrode by initial charge to form a lithium ion conductive film of the resultant oxidation product on the positive electrode.

Another aspect of the present invention provides a method of producing an alkali metal ion electric storage device including a positive electrode containing a positive electrode active material, a negative electrode containing a negative electrode active material constituted of C, Si, Sn, or Ge or an alloy containing at least one thereof, and an electrolytic solution.

A protective film of the oxidative decomposition product of the predoping material may be formed on the positive electrode by the initial charge.

DETAILED DESCRIPTION

Implementations of the present invention will now be described in detail.

The predoping material of the present invention is an alkali metal salt that can be applied to alkali metal ion electric storage devices, in particular, a lithium-ion rechargeable battery and a sodium-ion rechargeable battery and is represented by Formula (1):

R$(-$SM$)$n        (1)

In Formula (1), M represents lithium or sodium; n is an integer of 2 to 6; and R represents an aliphatic hydrocarbon having 1 to 10, preferably 2 to 6, carbon atoms, in particular, a $C_2$-$C_6$ alkane, or an optionally substituted aromatic hydrocarbon such as benzene, or an optionally substituted heterocycle, preferably 5-membered or 6-membered heterocycle, such as 2,4,6-triazine or alkylene carbonate.

Here, in a lithium-ion electric storage device, a predoping material of which M in Formula (1) is lithium is preferably used, whereas in a sodium-ion electric storage device, a predoping material of which M in Formula (1) is sodium is preferably used.

The predoping material of the present invention is preferably a small molecule having a molecular weight of 100 to 550, preferably, 290 to 420. When the number of lithium atoms per one molecule is two to six (n=2 to 6), the predoping performance per mass of the predoping material is advantageously high.

In initial charge/discharge (aging) in the present invention, the alkali metal ion electric storage device, including a positive electrode containing a positive electrode active material, a negative electrode containing a negative electrode active material constituted of C, Si, Sn, or Ge or an alloy containing at least one thereof, an electrolytic solution, and the predoping material, is charged and discharged with a voltage within a range (2 to 5 V) that is applied to the device in usual use.

As a result, the predoping material is electrochemically oxidized together with the positive electrode active material on the positive electrode and emits a large amount of alkali metal ions into the electrolytic solution.

The predoping material of the present invention is required to have a battery capacity density larger than that of the positive electrode active material. In the present invention, the predoping material has a capacity density larger than that of the positive electrode active material by 50 mAh/g or more, preferably, 100 mAh/g or more.

In the electric storage device of the present invention, the charge/discharge cycle characteristics and the input/output characteristics depend on the use area ($\Delta$SOC) of the negative electrode active material constituted of C, Si, Sn, or Ge or an alloy containing at least one thereof. Accordingly, the cycle characteristics and the input/output characteristics of the negative electrode material can be maximized by using a predoping material that can emit a large amount of lithium ions as described above.

Thus, the use of the predoping material of the present invention allows production of an alkali metal ion electric storage device having a high energy density and excellent cycle characteristics.

The predoping material of the present invention shows excellent alkali metal ion emitting ability in a state of being applied with a voltage in usual charge/discharge and contributes to an increase in charge efficiency, but is usually chemically stable as an alkali metal salt. Accordingly, even if the unreacted predoping material remains in the electric storage device, the safety is maintained.

As already described above, in conventional alkali metal ion electric storage devices, the irreversible capacity occurs by initial charge/discharge to reduce the energy density of the electric storage device. The alkali metal ion electric storage device of the present invention, however, has high capacity, that is, compensates the irreversible capacity with the predoping material that can emit a large amount of lithium ions, and thereby excellent electric storage performance is exhibited.

Figure 1A:
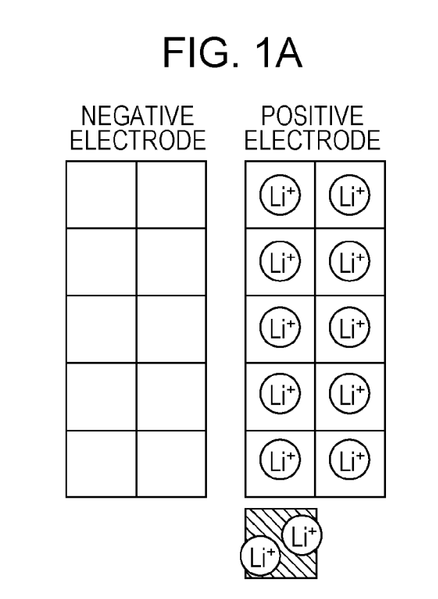
FIGS. 1A to 1C are schematic diagrams illustrating initial charge/discharge in a electric storage device of the present invention and the mechanism of increasing the charge/discharge capacity by the present invention.
Figure 1B:
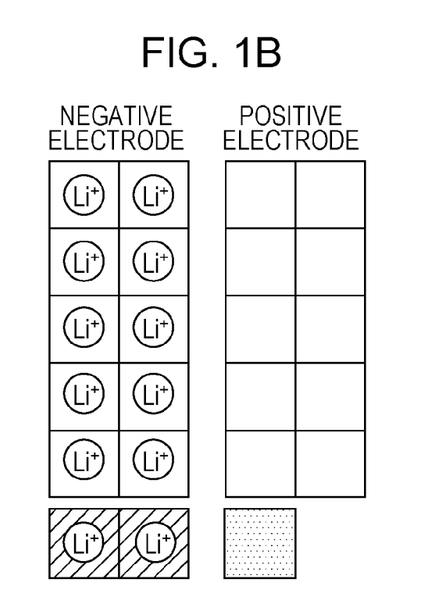
Figure 1C:
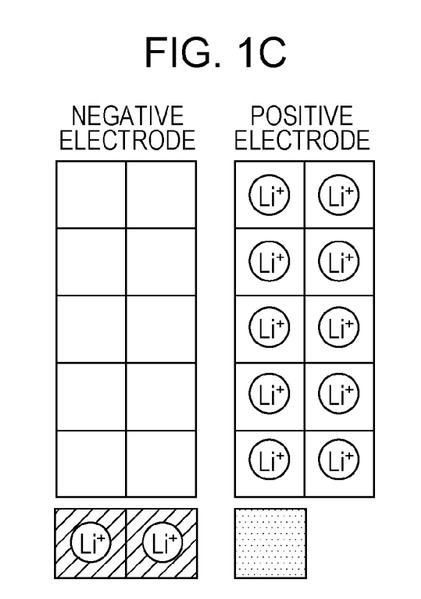

The initial charge/discharge of a electric storage device according to the present invention and the mechanism of increasing the charge/discharge capacity thereby will be described with reference to FIGS. 1A to 1C. In FIGS. 1A to 1C, a lithium-ion rechargeable battery will be described as an example, but the same mechanism adaptable to a sodium ion rechargeable battery.

FIG. 1A is a schematic diagram illustrating the state of lithium ions before the first charge, i.e., the state (initial state) at the time when a cell for lithium-ion electric storage device has been assembled. In the positive electrode, all of the lithium ion occlusion/emission sites (X) that can participate in charge/discharge are filled (doped) with lithium ions, whereas the negative electrode is in an undoped state.

In the electric storage device of the present invention, the predoping material (PD) represented by Formula (1) can be added to the electrolytic solution or the positive electrode.

FIG. 1B is a schematic diagram illustrating the state of lithium ions in the electric storage device after the first charge. That is, by the first charge against the electric storage device in the state shown in FIG. 1A, lithium ions are emitted from the lithium ion occlusion/emission sites (X) of the positive electrode active material and also emitted by the predoping material (PD) and are occluded in the lithium ion storage sites (Y) of the negative electrode to form the state shown in FIG. 1B.

The first charge is performed with a charging voltage that is usually applied to a lithium-ion electric storage device, i.e., within a range of 2 to 5 V. In the present invention, the reaction of the predoping material can be performed under the same conditions as those for the initial aging process that is performed in conventional electric storage devices. Therefore, a electric storage device having a high energy density can be produced without performing an additional production process.

As shown in FIG. 1C, by performing discharge, lithium ions are emitted from the negative electrode and are inserted into the occlusion/emission sites (X) of the positive electrode. The first discharge is performed with a discharging voltage that is usually applied to a lithium-ion electric storage device, i.e., within a range of 1 to 5 V.

A part of the lithium ions emitted on this occasion is consumed in the process of forming an SEI film (lithium ion conductive film) by reductive decomposition of the electrolytic solution (FIG. 1A).

In the present invention, the predoping material having a high capacity density and performing irreversible electrochemical reaction supplies lithium ions in an amount corresponding to the irreversible capacity of the negative electrode. Consequently, no storage site for useless lithium ions that cannot participate in charge/discharge reaction is generated in the positive electrode active material, and the charge/discharge capacities of the positive and negative electrodes are well balanced.

The predoping material is a material that does not usually receive lithium ions in the subsequent charge/discharge after Li ion emission, i.e., a chemically irreversible material.

The predoping material of the present invention emits lithium ions by, for example, oxidation reaction within a charging potential range and then preferably forms a lithium ion conductive protective film covering the positive electrode through, for example, polymerization reaction such as coupling reaction and does not participate in the charge/discharge reaction again. Specifically, it is believed that the predoping material (R—(S—Li+)n) of the present invention emits nLi$^+$, the remaining moiety ((R-nS—)) is apt to form a disulfide bond by coupling reaction (($2(R-S-))\rightarrow 2e^-$ + R—S—S—R) to form a high-quality positive electrode protective film having excellent lithium ion conductivity.

The predoping material of the present invention is preferably electrochemically irreversible, i.e., accomplishes the oxidation reaction within a voltage range that is applied to a electric storage device in usual use (i.e., performs rapid charge/discharge reaction).

The high-quality positive electrode protective film formed after lithium ion emission inhibits unnecessary oxidative decomposition reaction of the electrolytic solution on the positive electrode and facilitates the lithium ion removing/inserting process at the positive electrode due to its excellent lithium ion conductivity.

The compensation of irreversible capacity in the initial charge/discharge and the formation of a high-quality positive electrode protective film keep the high capacity retention also in the subsequent charge/discharge cycles. As a result, a electric storage device having a high energy density is provided.

The lithium-ion electric storage device of the present invention includes a positive electrode, a negative electrode, and nonaqueous electrolytic solution. An example of a lithium-ion rechargeable battery will now be described as an implementation of a electric storage device of the present invention with reference to drawings.

Figure 2:
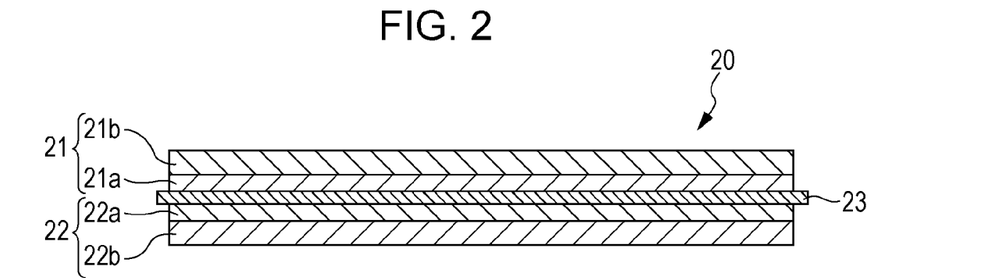
FIG. 2 is a schematic cross-sectional view illustrating an implementation of a electric storage device (lithium-ion rechargeable battery) of the present invention.

FIG. 2 is a schematic cross-sectional view illustrating an implementation of a lithium-ion rechargeable battery according to the present invention. As shown in the drawing, lithium-ion rechargeable battery 20 includes a positive electrode 21 and a negative electrode 22 disposed so as to face each other with a separator 23 therebetween.

The positive electrode 21 is constituted of a positive electrode mixture layer 21a containing a positive electrode material of the present invention and a positive electrode current collector 21b. The positive electrode mixture layer 21a is disposed on the separator 23 side of the positive electrode current collector 21b. The negative electrode 22 is constituted of a negative electrode mixture layer 22a and a negative electrode current collector 22b.

The negative electrode mixture layer 22a is disposed on the separator 23 side of the negative electrode current collector 22b. The positive electrode 21, the negative electrode 22, and the separator 23 are sealed in an outer container (not shown). The outer container is filled with a nonaqueous electrolytic solution. The outer container is made of, for example, a battery can or a laminate film. Each of the positive electrode current collector 21b and the negative electrode current collector 22b is optionally connected to a lead (not shown) for being connected to an external terminal.

Figure 3:
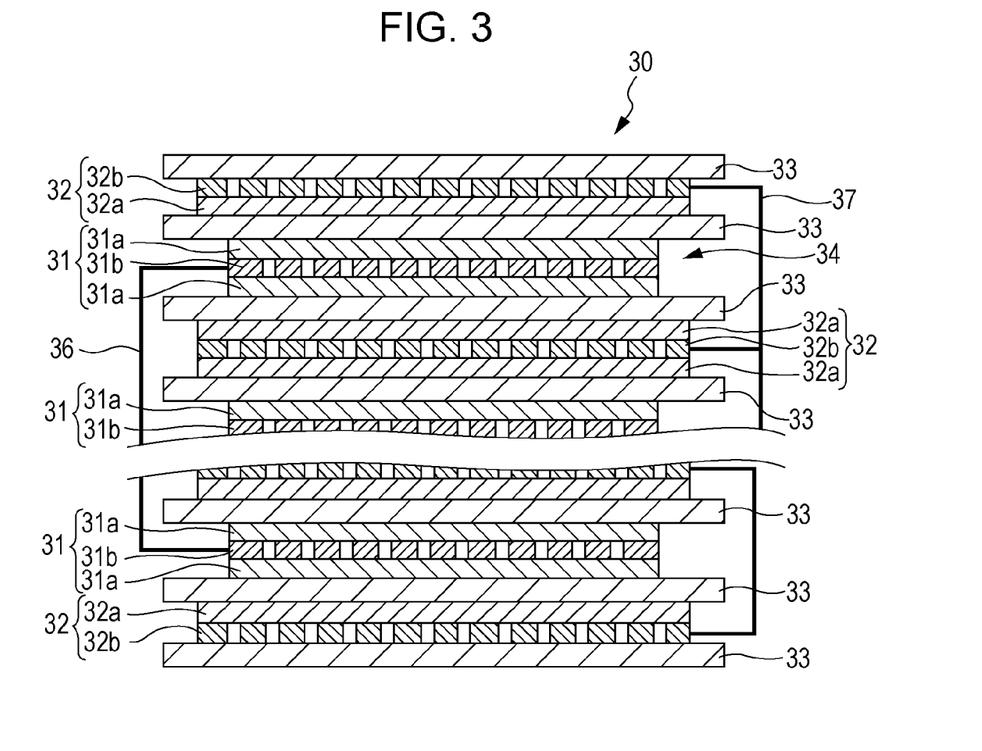
FIG. 3 is a schematic cross-sectional view illustrating another implementation of a electric storage device (lithium-ion rechargeable battery) of the present invention.

FIG. 3 is a schematic cross-sectional view illustrating another implementation of a lithium-ion rechargeable battery of the present invention. As shown in the drawing, lithium-ion rechargeable battery 30 includes an electrode unit 34 composed of positive electrodes 31 and negative electrodes 32 alternately stacked with separators 33 interposed therebetween. The positive electrodes 31 are each constituted of a positive electrode current collector 31b and positive electrode mixture layers 31a disposed on both surfaces of the positive electrode current collector 31b. The negative electrodes 32 are each constituted of a negative electrode current collector 32b and negative electrode mixture layers 32a disposed on both surfaces of the negative electrode current collector 32b (provided that in each of the uppermost and the lowermost negative electrodes 32, the negative electrode mixture layer 32a is disposed on one surface of the negative electrode current collector 32b).

The positive electrode current collector 31b has a projection (not shown), the projections of multiple positive electrode current collectors 31b are superposed, and a lead 36 is welded to the superposed portions. The negative electrode current collector 32b also has a similar projection, the projections of multiple negative electrode current collectors 32b are superposed, and a lead 37 is welded to the superposed portions. The lithium-ion rechargeable battery 30 is constituted by sealing the electrode unit 34 and a nonaqueous electrolytic solution in an outer container (not shown) such as a laminate film. The leads 36 and 37 are exposed to the outside of the outer container for being connected to external equipment.

In the lithium-ion rechargeable battery 30, the uppermost and the lowermost electrodes are negative electrodes, but the configuration is not limited thereto. The uppermost and the lowermost electrodes may be positive electrodes.

Production of Positive Electrode

The positive electrode of the present invention is not particularly limited and can be produced using a known material. Specifically, the positive electrode is produced as follows.

In the present invention, the positive electrode active material may be made of any material and can be made of a known positive electrode active material.

For example, the positive electrode active material can be a spinel compound represented by composition formula $LiM^1_{0.5}M^2_{1.5}O_4$ (M represents a metal atom) such as spinel nickel manganese ($LiNi_{0.5}Mn_{1.5}O_4$); a spinel compound represented by composition formula $LiM_2O_4$ (M represents a metal atom) such as lithium manganate ($LiMn_2O_4$); a $LiMO_2$ (M represents a metal atom) layered oxide such as lithium cobaltate ($LiCoO_2$), lithium nickelate ($LiNiO_2$), lithium manganese dioxide ($LiMnO_2$), or $LiNi_{0.5}Mn_{0.50}O_2$; an olivine compound represented by composition formula $LiMPO_4$ (M represents a metal atom) such as lithium manganese phosphate ($LiMnPO_4$), lithium iron phosphate ($LiFePO_4$), or lithium cobalt phosphate ($LiCoPO_4$); a solid solution compound represented by composition formula $Li_2MO_3$ (M represents a metal atom) such as a solid solution of $Li_2MnO_3$ with Fe or Ni; a silicate compound represented by composition formula $Li_2MSiO_4$ (M represents a metal atom) such as lithium iron silicate ($Li_2FeSiO_4$), lithium manganese silicate ($Li_2MnSiO_4$), lithium cobalt silicate ($Li_2CoSiO_4$), or lithium nickel silicate ($Li_2NiSiO_4$); a vanadium oxide compound such as vanadium pentoxide ($V_2O_5$); a polyanion compound such as lithium vanadium phosphate (e.g., $Li_3V_2(PO_4)_3$); or a sulfur compound such as inorganic sulfur ($S_8$) or lithium sulfide ($Li_2S$); or a mixture of two or more thereof. It is possible to use a material other than the above-mentioned materials or a mixture of any of the above-mentioned materials and another material as the positive electrode active material.

In the present invention, in particular, a high-voltage compound such as lithium vanadium phosphate (e.g., $Li_3V_2(PO_4)_3$) is preferably used.

In the electric storage device of the present invention, addition of a predoping material is indispensable. The predoping material may be added to the positive electrode. In particular, when the predoping material is hardly soluble or insoluble in the electrolytic solution, that is, when, for example, $Li_3BTTA$ is used, the predoping material is preferably added to the positive electrode.

When the predoping material is added to the positive electrode, the ratio of the predoping material to the positive electrode active material is 0.01% to 20% by mass and preferably 10% to 16% by mass. Within this range, the feature of the predoping material, i.e., high irreversible capacity, can be utilized, and a reduction in capacity density due to excessive addition can be avoided. As a result, an alkali metal ion electric storage device having a high energy density is constituted.

The predoping material used in the present invention is represented by Formula (1):

$$R\text{---}(SM)_n \qquad (1)$$

in which M represents lithium or sodium; n is an integer of 2 to 6; and R represents an aliphatic hydrocarbon having 1 to 10, preferably 2 to 6, carbon atoms, in particular, a $C_2$-$C_6$ alkane, or an optionally substituted aromatic hydrocarbon such as benzene, or an optionally substituted heterocycle, preferably 5-membered or 6-membered heterocycle, such as 2,4,6-triazine or alkylene carbonate. The predoping material may be a commercially available compound.

More specifically, preferred predoping materials are as follows.

TABLE 1

| | Structure | Name | Abbreviation | MW | Number of reaction electrons | Theoretical capacity |
|---|---|---|---|---|---|---|
| 1 | (structure: 1,3,5-triazine with three SLi groups) | Lithium 1,3,5-triazine-2,4,6-tris(thiolate) | Li3TTTA | 195 | 3 | 412 |
| 2 | (structure: benzene with three SLi groups at 1,3,5) | Lithium benzene-1,3,5-tris(thiolate) | Li3BTTA | 192 | 3 | 419 |
| 3 | (structure: benzene with six SLi groups) | Lithium benzene-1,2,3,4,5,6-hexa(thiolate) | Li6BHTA | 306 | 6 | 525 |
| 4 | LiS–(CH2)4–SLi | Lithium butane-1,4-bis(thiolate) | Li2BBTA | 134 | 2 | 400 |
| 5 | (structure: 2-oxo-1,3-dioxolane-4,5-bis(thiolate) Li salt) | Lithium 2-oxo-1,3-dioxolane-4,5-bis(thiolate) | Li2ODBTA | 164 | 2 | 327 |
| 6 | (structure: 2-oxo-1,3-dioxolane-4,5-bis(thiolate) Na salt) | Sodium 2-oxo-1,3-dioxolane-4,5-bis(thiolate) | Na2ODBTA | 196 | 2 | 291 |

A binder is used for forming the positive electrode mixture layer. For example, the binder can be a fluorine-containing resin such as polyvinylidene fluoride, an acrylic binder, a rubber binder such as SBR, a thermoplastic resin such as polypropylene or polyethylene, or carboxymethyl cellulose. The binder is preferably a fluorine-containing resin or a thermoplastic resin, which are chemically and electrochemically stable against the nonaqueous electrolytic solution used in the electric storage device of the present invention, and a fluorine-containing resin is particularly preferred. Examples of the fluorine-containing resin include polyvinylidene fluoride, polytetrafluoroethylene, vinylidene fluoride-3-ethylene fluoride copolymers, ethylene-4-ethylene fluoride copolymers, and propylene-4-ethylene fluoride copolymers. The amount of the binder is preferably 0.5 to 20% by mass based on the amount of the positive electrode mixture.

A conductive assistant is used for forming the positive electrode mixture layer. For example, the conductive assistant can be conductive carbon such as Ketjen black, a metal such as copper, iron, silver, nickel, palladium, gold, platinum, indium, or tungsten, or a conductive metal oxide such as indium oxide or tin oxide. The amount of the conductive assistant is preferably 1% to 30% by mass based on the amount of the positive electrode active material.

A solvent is used for forming the positive electrode mixture layer. For example, the solvent can be water, isopropyl alcohol, N-methylpyrrolidone, or dimethylformamide.

The positive electrode current collector may be a conductive substrate of which surface in contact with the positive electrode mixture layer has conductivity. For example, the conductive substrate can be a substrate made of a conductive material such as a metal, a conductive metal oxide, or a conductive carbon or a non-conductive substrate coated with a conductive material mentioned above. The conductive material is preferably copper, gold, or aluminum or an alloy thereof or conductive carbon.

The material mentioned above as the positive electrode current collector may be in a form of an expand metal, a punching metal, foil, a net, or foam. When the positive electrode current collector is a porous material, the shape and the number of the through-holes are not particularly limited and may be appropriately determined within ranges that do not prevent the transfer of lithium ions.

The positive electrode mixture layer is formed by a process including applying, onto the positive electrode current collector, a positive electrode slurry prepared by dispersing a mixture containing the positive electrode material, the binder, and the conductive assistant in a solvent and drying it.

In a case of adding a predoping material to the positive electrode material, a slurry is prepared by adding the positive electrode material, the binder, the conductive assistant, and the predoping material to a solvent as in above and is formed into a positive electrode mixture layer.

Alternatively, a slurry containing the predoping material only is prepared and may be applied to the surface of a positive electrode mixture layer formed of a mixture of the positive electrode material, the binder, the conductive assistant, and a solvent. In this case, however, it is necessary to pay attention to an excessive increase in charge transfer resistance at the positive electrode/electrolytic solution interface and a decrease in mechanical strength of the electrode due to binder migration.

The thus-prepared positive electrode mixture layer disposed and dried on the current collector may be then subjected to pressing or other processing. As a result, the positive electrode mixture layer is uniformly and strongly press-bonded to the current collector. The positive electrode mixture layer has a thickness of 10 to 200 µm and preferably 20 to 100 µm.

Production of Negative Electrode

The negative electrode of the present invention can be produced using a known material.

The negative electrode active material may be any material into which lithium ions or sodium ions can be removably inserted. For example, the negative electrode active material can be a silicon material such as silicon or a silicon alloy; a tin material; a lithium intercalation carbon material such as graphite, hardly graphitizable carbon, or easily graphitizable carbon; a polyacene material; a lithium metal material such as a lithium alloy (e.g., Li—Al alloy); or a lithium compound (e.g., lithium nitride) such as an intermetallic compound of a lithium metal and another metal (e.g., intermetallic compound containing tin, silicon, or another metal). The lithium intercalation carbon material is a material that can reversibly dope lithium ions. For example, the polyacene material can be PAS having a polyacene skeleton and being insoluble and infusible.

In the present invention, a silicon material or a carbon material is preferably used, and a carbon material is particularly preferred. The negative electrode active material may be a single material or a mixture of two or more materials.

In the production of the negative electrode of the present invention, a negative electrode mixture layer is formed by, for example, applying, onto the negative electrode current collector, a negative electrode slurry prepared by dispersing a mixture containing the negative electrode active material and the binder in a solvent and drying it. The binder, the solvent, and the current collector may be those described in the positive electrode.

The negative electrode mixture layer usually has a thickness of 10 to 200 µm and preferably 20 to 100 µm.

In the present invention, the areal weight of the negative electrode mixture layer is appropriately designed depending on the areal weight of the positive electrode mixture layer. In general, in a lithium-ion rechargeable battery, from the viewpoints of the balance in the capacity between the positive and negative electrodes and the energy density, the battery is designed such that the capacity (mAh) of the positive electrode is approximately the same as that of the negative electrode. Accordingly, the areal weight of the negative electrode mixture layer is designed based on the type of the negative electrode active material, the capacity of the positive electrode, and other factors.

Nonaqueous Electrolytic Solution

The nonaqueous electrolytic solution in the present invention is not particularly limited and may be a known material. For example, from the viewpoints of not causing electrolysis even at a high voltage and allowing lithium ions to be stably present, an electrolytic solution prepared by dissolving a typical lithium salt as an electrolyte in an organic solvent can be used.

Examples of the electrolyte include $LiSO_3CF_3$, $LiSO_8C_4F_9$, $LiN(SO_2CF_3)_2$, $LiC(SO_2CF_3)$, $LiC_4BO_8$, $LiBF_4$, $LiPF_6$, and $LiClO_4$ and mixtures of two or more thereof.

As the solvent for the nonaqueous electrolytic solution, a solvent mainly composed of a carbonate component is used. For example, the solvent can be a linear carbonate such as a dimethyl carbonate (DMC), diethyl carbonate (DEC), or ethyl methyl carbonate (EMC); a cyclic carbonate such as ethylene carbonate (EC), propylene carbonate (PC), butylene carbonate (BC), or vinylene carbonate (VC); a solvent having a relatively small molecular weight such as acetonitrile (AN), 1,2-dimethoxyethane (DME), tetrahydrofuran (THF), 1,3-dioxolane (DOXL), dimethyl sulfoxide (DMSO), sulfonane (SL), or propionitrile (PN); or a mixture thereof. A mixture of a linear carbonate and a cyclic carbonate is particularly preferred. In addition, the solvent may be a mixture of two or more linear carbonates and two or more cyclic carbonates. The solvent optionally contains, for example, fluoroethylene carbonate (FEC).

The concentration of the electrolyte in the nonaqueous electrolytic solution is preferably 0.1 to 5.0 mol/L and more preferably 0.5 to 3.0 mol/L.

The nonaqueous electrolytic solution may be a solution or may be formed into a solid electrolyte or polymer gel electrolyte by being mixed with a plasticizer, a polymer, or another material.

The electrolytic solution may contain a predoping material that is soluble therein. For example, an electrolyte, a solvent for electrolytic solution, and a predoping material may be simultaneously mixed, or a predoping material may be added to an electrolytic solution prepared in advance. The molar ratio of the predoping material to the total amount of the electrolytic solution is preferably 0.04 to 0.25. In this range, the predoping material does not precipitate even at low temperature, and an alkali metal ion electric storage device having a high energy density is constituted.

Separator

In the present invention, any separator can be used without particular limitation, and a known separator can be used. A preferred separator is, for example, a porous material with communication pores not having electron conductivity and having durability against the electrolytic solution, the positive electrode active material, and the negative electrode active material. Examples of such a porous material include woven fabric, nonwoven fabric, synthetic resin fine porous films, and glass fibers. The synthetic resin fine porous films are preferred, and a fine porous film made of polyolefin such as polyethylene or polypropylene is particularly preferred from its thickness, film strength, and film resistance.

EXAMPLES

The present invention will now be more specifically described by examples, but is not limited to the following examples.

I. Production of Electric Storage Device

Example 1

(1) Production of Positive Electrode
(1-1) Positive Electrode Mixture
A positive electrode mixture was prepared from the following materials:
Lithium vanadium phosphate ($Li_3V_2(PO_4)_3$): 90 parts by mass,
Polyvinylidene fluoride (PVdF): 5 parts by mass,
Carbon black: 5 parts by mass, and
N-Methyl-2-pyrrolidone (NMP): 100 parts by mass.
The positive electrode active material ($Li_3V_2(PO_4)_3$) and other materials were mixed to prepare a positive electrode mixture slurry.
The positive electrode mixture slurry was applied to aluminum foil (thickness: 10 μm) as the positive electrode current collector at a thickness of 100 μm by a doctor blade method and was dried to form a positive electrode mixture layer on the positive electrode current collector. The areal weight (on one surface) of the positive electrode mixture layer was 15 mg/cm$^2$.
(1-2) Preparation of Predoping Material Dispersion
A predoping material dispersion was prepared from the following materials:
$Li_3BTTA$: 16 parts by mass, and
Methanol (MeOH): 84 parts by mass.
A predoping material dispersion was prepared by dispersing a predoping material ($Li_3BTTA$ (Compound 2 in Table 1)) in the solvent shown above and was cast on the positive electrode mixture layer. The mass of the predoping material cast was 0.0016 g, and the amount of the predoping material ($Li_3BTTA$) relative to the amount of the positive electrode active material (LVP) was 11.7% by mass. The dispersion applied to the positive electrode mixture layer was dried at room temperature under vacuum for 24 hours.
(2) Production of Negative Electrode
A negative electrode mixture slurry was prepared from the following materials:
Graphite (C): 90 parts by mass,
SBR: 3 parts by mass,
Sodium carboxymethylcellulose: 2 parts by mass
Carbon black: 5 parts by mass, and
Solvent (water): 100 parts by mass.
The negative electrode active material (C) and other materials were mixed to prepare a negative electrode mixture slurry.
The negative electrode mixture slurry was applied to copper foil as the negative electrode current collector and was dried to obtain a negative electrode mixture in a disk shape having a diameter of 15 mm.
(3) Preparation of Electrolytic Solution
Lithium hexafluorophosphate ($LiPF_6$) was dissolved in 70 parts by volume of ethylene carbonate (EC), 20 parts by volume of dimethyl carbonate (DMC), 5 parts by volume of ethyl methyl carbonate (EMF), and 5 parts by volume of fluoroethylene carbonate (FEC) to give an electrolytic solution containing 1.2 M of lithium hexafluorophosphate.
(4) Production of Lithium-ion Rechargeable Battery
A lithium-ion rechargeable battery as in an implementation shown in FIG. 2 was produced using the positive electrode mixture, the negative electrode mixture, and the electrolytic solution prepared above and a polyethylene separator. Specifically, the positive electrode mixture and the negative electrode mixture were stacked with a polyethylene separator having a thickness of 25 mm therebetween. The laminate including the positive electrode and the negative electrode and the electrolytic solution were introduced into a CR2032-type coin cell.
As a result, a lithium-ion rechargeable battery of the present invention was produced.

Comparative Example 1

The same procedure as in Example 1 was performed except that the positive electrode did not contain the pre-doping material. As a result, a lithium-ion rechargeable battery for comparison was produced.

Examples 2 and 3

(1) Production of Carbon Electrodes Containing a Predoping Material $Li_3BTTA$ or $Li_2BBTA$
An electrode slurry was prepared from the following materials:
Carbon fibers: 90 parts by mass,
SBR: 3 parts by mass,
Sodium carboxymethylcellulose: 2 parts by mass
Carbon black: 5 parts by mass, and
Solvent (water): 100 parts by mass.
These materials were mixed to prepare an electrode slurry. This slurry was applied to a current collector and was dried to give a carbon electrode mixture in a disk shape having a diameter of 13 mm. A predoping material dispersion prepared as in Example 1 was dropwise added to the carbon electrode mixture, followed by drying in vacuum for 24 hours.
As the predoping material, lithium benzene-1,3,5-tris (thiolate) ($Li_3BTTA$ (Compound 2 in Table 1): Example 2) or lithium butane-1,4-bis(thiolate) ($Li_2BBTA$ (Compound 4 in Table 1): Example 3) was used.
(2) Preparation of Electrolytic Solution
An electrolytic solution was prepared as in Example 1.
(3) Production of Battery
Batteries were each produced using the carbon electrode produced above, lithium metal foil, the electrolytic solution, and an ethylene separator. Specifically, the carbon electrode and a Li metal were stacked with a polyethylene separator having a thickness of 25 mm therebetween. This laminate and the electrolytic solution were introduced in a CR2032-type coin cell.

II. Electrochemical Characteristics and Predoping Effect of Predoping Material (1) Measurement and Evaluation of Electric Storage Performance of Lithium-ion Electric Storage Device
The lithium-ion rechargeable batteries produced in Example 1 and Comparative Example 1 were charged under constant current and constant voltage of a current of 0.1 C until a voltage of 4.6 V for 12 hours with TOSCAT-3100 available from Toyo System Co., Ltd. The batteries were then discharged at a 0.1 C constant current until the voltage reached 2.5 V.
The measured data of charge/discharge of the batteries in Example 1 and Comparative Example 1 are shown in the graph of FIG. 4.

Figure 4:
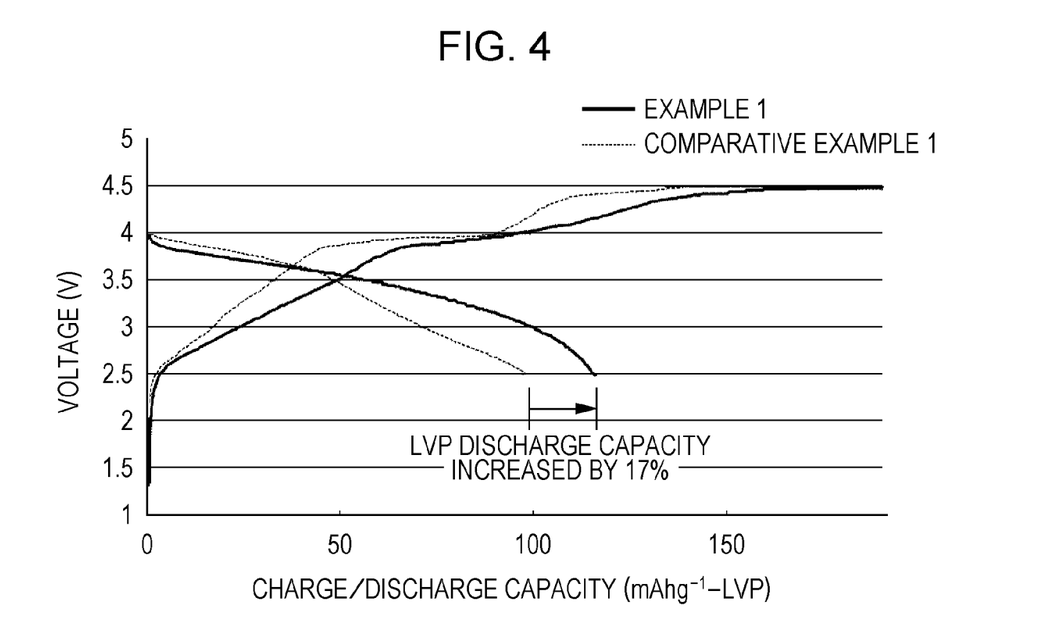
FIG. 4 is a graph showing charge/discharge capacity (measured values) of a lithium-ion rechargeable battery in an implementation of the present invention and a lithium ion rechargeable battery for comparison.

FIG. 4 demonstrates that the initial discharge capacity in Example 1 was larger than that in Comparative Example 1 by 17%.

It is believed that the increase in initial discharge capacity was caused by that Li₃BTTA was electrochemically oxidized in the first charging process and thereby emitted a large amount of lithium ions to increase the amount of lithium ions capable of participating in the subsequent discharge reaction and, as a result, the discharge capacity was increased.

Furthermore, the increase is believed to be caused by occurrence of coupling reaction (disulfide bond generating reaction) of the cations generated from Li₃BTTA after the emission of lithium ions.

Table 2 shows (1) the amount (g) of the predoping material (Li₃BTTA) in the positive electrode active material (LVP), (2) theoretical capacity (per amount) of the predoping material, (3) measured value of charging capacity (mAh), (4) measured value of discharging capacity (mAh), (5) difference (increase) in charging capacity (mAh) from that in Comparative Example 1, and (6) difference (increase) in discharging capacity (mAh) from that in Comparative Example 1.

TABLE 2

| Example | Amount of Li₃BTTA (g) | Theoretical capacity/mAh | Charging capacity/mAh | Discharging capacity/mAh | Difference in charging capacity/mAh | Difference in discharging capacity/mAh |
|---|---|---|---|---|---|---|
| Example 1 | 0.0014 | 0.60 | 2.90 | 1.61 | 0.53 | 0.22 |
| Comparative Example 1 | — | — | 2.37 | 1.39 | — | — |

(2) Measurement and Evaluation of Performance of Lithium Ionic Additive

Figure 5:
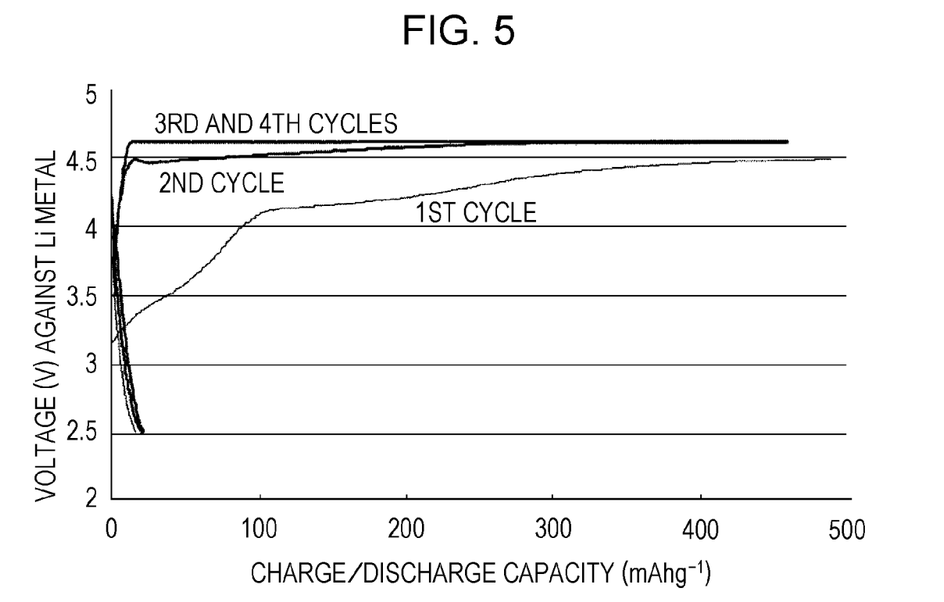
FIG. 5 is a graph showing the charge/discharge reaction behavior of a predoping material (lithium benzene-1,3,5-tris (thiolate): $Li_3BTTA$) of the present invention.

The lithium-ion electric storage device in Example 2 was charged under constant current and constant voltage of a current of 0.1 C until a voltage of 4.6 V for 12 hours with TOSCAT-3100 available from Toyo System Co., Ltd. The electric storage device was then discharged at a 0.1 C constant current until the voltage reached 2.5 V (initial four cycles). The measurement results are shown in the graph of FIG. 5.

Figure 6:
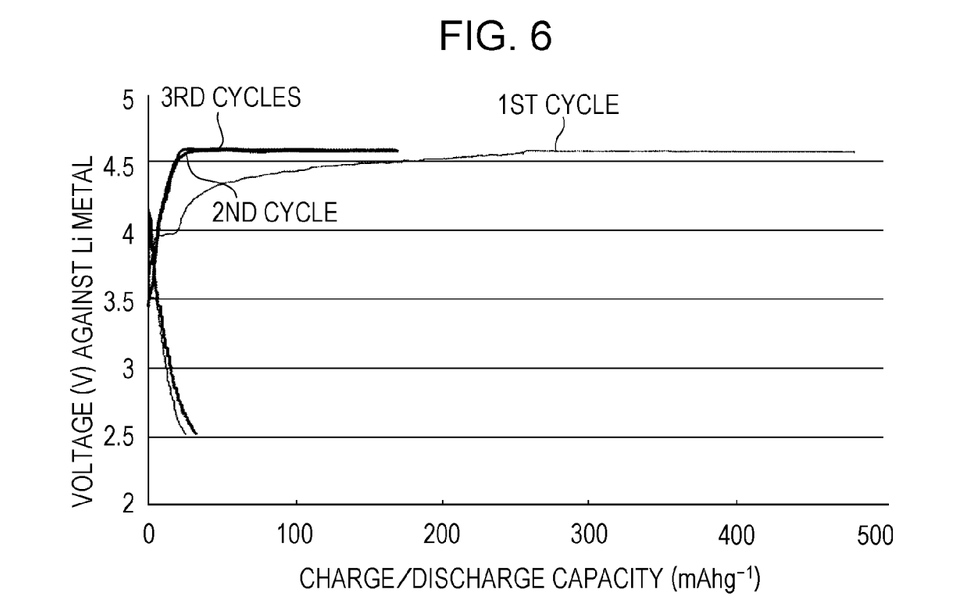
FIG. 6 is a graph showing the charge/discharge reaction behavior of a predoping material (lithium butane-1,4-bis (thiolate): $Li_2BBTA$) of the present invention.

The lithium-ion electric storage device in Example 3 was subjected to three cycles of initial charge/discharge as in above. The measurement results are shown in the graph of FIG. 6.

It was observed in both electric storage devices of Examples 2 and 3 that the charging capacity caused by oxidation reaction of the predoping material was larger than the discharge capacity and that the reaction irreversibly progressed. It was also observed that the resulting charging capacity decreased with repetition of the charge/discharge cycle and that the oxidation reaction of the predoping material converged without side reaction. These results demonstrate that Li₃BTTA and Li₂BBTA can supply an excessive amount of lithium ions into a electric storage device as expected, i.e., they have ideal redox properties as predoping materials.

The present invention is not limited to the above-described configurations of the implementations and examples, and various modifications are possible within the range of the gist of the invention.

The invention claimed is:

1. A predoping material for an alkali metal ion electric storage device, wherein the predoping material is represented by Formula (1):

wherein, M represents lithium or sodium; n represents an integer of 2 to 6; and R represents an aliphatic hydrocarbon, optionally substituted aromatic hydrocarbon, or optionally substituted heterocycle having 1 to 10 carbon atoms.

2. The predoping material for an alkali metal ion electric storage device according to claim 1, wherein R represents a linear or branched C2-C6 alkane, triazine, benzene, or C2-C6 alkylene carbonate.

3. The predoping material for an alkali metal ion electric storage device according to claim 1, the predoping material having a molecular weight of 100 to 550.

4. The predoping material for an alkali metal ion electric storage device according to claim 2, the predoping material having a molecular weight of 100 to 550.

5. An alkali metal ion electric storage device comprising:
a positive electrode containing a positive electrode active material;
a negative electrode containing a negative electrode active material constituted of C, Si, Sn, or Ge or an alloy containing at least one thereof;
an electrolytic solution; and
a predoping material according to claim 1.

6. The alkali metal ion electric storage device according to claim 5, wherein the predoping material is contained in the electrolytic solution.

7. The alkali metal ion electric storage device according to claim 6, wherein the electrolytic solution contains 0.04% to 0.25% by mol of the predoping material.

8. The alkali metal ion electric storage device according to claim 5, wherein the predoping material is contained in the positive electrode.

9. The alkali metal ion electric storage device according to claim 8, wherein the ratio of the predoping material to the positive electrode active material is 0.01% to 20% by mass.

10. The alkali metal ion electric storage device according to claim 5, wherein the predoping material has a capacity density larger than that of the positive electrode active material by 50 mAh/g or more.

11. The alkali metal ion electric storage device according to claim 5, wherein the predoping material is oxidatively decomposed on the positive electrode by initial charge to form a film of the resultant decomposition product covering the positive electrode.

12. A method of producing an alkali metal ion electric storage device including a positive electrode containing a positive electrode active material, a negative electrode containing a negative electrode active material constituted of C, Si, Sn, or Ge or an alloy containing at least one thereof, and an electrolytic solution, the method comprising:

performing initial charge in the presence of a predoping material according to claim 1 to oxidatively decompose the predoping material on the positive electrode.

13. The method of producing an alkali metal ion electric storage device according to claim 12, wherein a film of an oxidative decomposition product of the predoping material is formed on the positive electrode by the initial charge.

* * * * *